United States Patent [19]

Ushiro

[11] 4,263,400
[45] Apr. 21, 1981

[54] IMMOBILIZED ENZYMES

[75] Inventor: Soichiro Ushiro, Kokubunji, Japan

[73] Assignee: CPC International Inc., Englewood Cliffs, N.J.

[21] Appl. No.: 2,839

[22] Filed: Jan. 11, 1979

[30] Foreign Application Priority Data

May 12, 1978 [JP] Japan .................................. 53-55691

[51] Int. Cl.³ ...................... C12N 11/02; C12P 19/24; C12N 9/92
[52] U.S. Cl. ...................................... 435/177; 435/94; 435/179; 435/180; 435/234; 435/815
[58] Field of Search ................ 435/94, 174, 177, 178, 435/179, 180, 902, 234; 426/814, 815

[56] References Cited

U.S. PATENT DOCUMENTS

| | | | |
|---|---|---|---|
| 3,625,828 | 12/1971 | Brownewell | 435/902 X |
| 3,708,397 | 1/1973 | Sipos | 435/179 X |
| 3,909,354 | 9/1975 | Thompson et al. | 435/179 |
| 3,956,065 | 5/1976 | Idaszak et al. | 435/94 |

FOREIGN PATENT DOCUMENTS

1371489 10/1974 United Kingdom ..................... 435/94

*Primary Examiner*—David M. Naff

[57] ABSTRACT

When immobilizing enzymes such as glucose isomerase by adsorption on a carrier such as an ion exchange resin, the enzyme prior to adsorption on the carrier is separated from a high molecular weight, non-dialyzable polysaccharide which inhibits adsorption of the enzyme to the carrier.

10 Claims, 1 Drawing Figure

Fig. 1 DEAE-Cellulose Column Chromatography of Glucose Isomerase Solution S

IMMOBILIZED ENZYMES

BACKGROUND OF THE INVENTION

In recent years there has been heavy emphasis on the development and industrial application of processes which involve the use of immobilized enzyme. Immobilized enzyme is generally produced by contacting an enzyme preparation (either a crude or purified solution of the enzyme) with an adsorptive carrier therefor. These immobilized enzymes are particularly useful because they facilitate continuous as opposed to batch processing.

In attempting to adapt various enzymes for immobilized enzyme usage, however, certain problems such as low levels of absorption on the carrier have been encountered. This problem is particularly undesirable because it results in immobilized enzyme compositions having low operational efficiencies.

The present invention involves, in part, the discovery of a major cause of and of means for overcoming the foregoing problem. Consequently, this invention permits use of many enzymes which have not heretofore been successfully or practicably employed in immobilized form.

The difficulties heretofore encountered in the immobilization of certain enzymes have been found to derive from the presence of certain polysaccharides of high molecular weight which are commonly present in enzyme preparations. These polysaccharides are also adsorbed by carriers and have been found to inhibit the adsorption of the enzyme, presumably through blockage of active sites on a carrier which would normally attract and hold the enzyme.

SUMMARY OF THE INVENTION

The present invention involves a method for the production of immobilized enzyme comprising:
(a) obtaining an enzyme preparation containing adsorption-inhibiting polysaccharide;
(b) separating polysaccharide from the enzyme preparation; and
(c) contacting the resultant enzyme solution with an adsorbtive carrier to immobilize the enzyme.

This invention provides a method for easily obtaining an immobilized enzyme of high activity and with which it is possible to carry out continuous reactions at increased efficiency.

DETAILED DESCRIPTION OF THE INVENTION

Although not all enzyme preparations contain enough polysaccharide to evidence substantial interference with enzyme adsorption and immobilization on a carrier, many do. In particular, those microorganisms which produce and retain enzymes substantially intracellularly are a problem. In order to obtain an enzyme preparation therefrom, it is necessary to effect cell rupture in order to release enzyme. This rupture has been found to contribute significantly to the amount of adsorption-inhibiting polysaccharide which will be present in a resultant enzyme preparation.

It has also been discovered that preparations of certain types of enzyme appear to evidence higher concentrations of adsorption-inhibiting polysaccharide. In particular, preparations of glucose isomerase enzyme generally contain significant amounts of adsorption-inhibiting polysaccharide. As a consequence, the present invention is particularly useful for immobilization of glucose isomerase and still more particularly useful where that glucose isomerase preparation has been obtained from a microorganism, such as an Actinomycetes microbe of the Streptomyces family or a bacterium including those from the Lactobacillus family, particularly *L. brevis*, which produces enzyme intracellularly.

An enzyme preparation is readily obtained from microorganisms which produce enzyme extracellularly by means known in the art. For these microorganisms, it is customary merely to remove the cells (by filtration, centrifugation, or the like) from the medium containing the enzyme. The remaining medium is a suitable preparation.

For intracellularly producing microorganisms, it is necessary first to separate the enzyme from the cells of the microorganisms. Exemplary methods for carrying out this separation are described in U.S. Pat. Nos. 3,708,397; 3,850,751; and 3,868,304. Thus, the cells are ruptured normally by autolysis (or treatment with supersonic waves) grinding, acid lysis, or the like. Thereafter, filtration may be employed to remove cellular debris, leaving an enzyme preparation containing the adsorption-inhibiting polysaccharide.

Where desired, the crude enzyme preparation obtained directly from the culture medium or the microorganisms themselves may be purified by conventional technique. For example, the crude preparation may be treated with protamine or the like to precipitate and eliminate nucleic acids. Preparations also may, and commonly are, subjected to concentration. This produces extract having a greater unit activity and also may further reduce contaminants. Incident to these conventional purification treatments for crude preparations, however, adsorption-inhibiting polysaccharide remains in the preparation, generally at a level of up to several percent or more relative to the protein weight of enzyme. This polysaccharide—the existence and effect of which are not believed to have been appreciated—must be essentially completely removed to allow maximum enzyme adsorption.

The precise character of these polysaccharides may vary with source. They are, therefore, best described simply by their abilities to be adsorbed by conventional enzyme carriers and inhibit (or interfere) with the adsorption of enzyme. In addition, however, they may generally be characterized as being of high molecular weights and non-dialyzable.

To separate polysaccharide from a crude or purified enzyme preparation, a variety of techniques is suitable. Polysaccharide may, for example, be separated and eliminated from the preparation through contact with an ion exchange resin which will selectively adsorb the polysaccharide while remaining essentially inert toward the enzyme. Alternatively, an organic solvent may be added to the preparation at a concentration sufficient to precipitate the enzyme selectively. Precipitated enzyme may then be dissolved in a solvent such as water to produce a reconstituted enzyme solution essentially free of adsorption-inhibiting polysaccharide. Similarly, a salt may be added to the preparation at a concentration sufficient to selectively precipitate enzyme, which may then be redissolved to produce the desired, polysaccharide-free solution.

Adsorbents which can selectively remove polysaccharides (while adsorbing little or no enzyme) and can be employed for the purpose of separating polysaccharide from a given enzyme solution include: anion exchange resins such as strongly basic anion exchange resins (type I), strongly basic anion exchange resins (type II), moderately-basic anion exchange resins, and weakly-basic anion exchange resins. Exemplary resins are set forth in *Ion Exchange Resins,* R. Kunin and R. J. Myers, John Wiley & Sons 1952, and in "DIAION-Manual of Ion Exchange Resins", a brochure of Mitsubishi Chemical Industries Ltd. However, it is possible to employ any material which adsorbs little or none of the enzyme, but is capable of selectively adsorbing and eliminating the polysaccharides existing in the enzyme solution. Suitable further adsorbents may be identified by routine testing in the manner set forth in the examples below.

Examples of specifically preferred resins are Lewatit MP-500, Lewatit M-504, Lewatit CA-9268HL (all of the foregoing are brand names of resin products of Bayer Co., Ltd., of West Germany), IMAC A-27, IMAC S5-40, and IMAC S5-50 (all of the foregoing are brand names of resin products of Shinetsu Kagaku Co., Ltd.). The exchange groups of the above-mentioned ion exchange resins include any of OH, Cl, $SO_4$ and the like, but it is preferable that the exchange groups be Cl desirably originating from NaCl or HCl.

When separating saccharide from enzyme with anion-exchange resin, the enzyme preparation should normally have a concentration of from 100 IGIU/ml to 5,000 IGIU/ml, preferably about 500 IGIU/ml. Such a concentration may be obtained by dilution or concentration, as required. The solution is then simply contacted with the above-mentioned ion exchange resin in a column or some other suitable vessel.

Regarding the activity of the enzyme, the term "IGIU" is an abbreviation for International Glucose Isomerase Unit. One IGIU of the enzyme is defined as that amount which produces (in, for example, the case of glucose isomerase) 1 micromole of fructose per minute, in a 0.1 molar solution of glucose at pH 7.5 and 60° C. in the presence of 0.01 molar $MgCl_2$ and 0.001 molar $CoCl_2$, using the following assay procedure, involving making a spectrophotometric determination of the ketose produced from a glucose solution under a standardized set of conditions.

A stock solution is made up in the following manner:

| Stock Solution for Assay | |
|---|---|
| Component | Amount |
| 0.01 M $MgCl_2$ | 1 ml |
| 0.001 M $CoCl_2$ | 1 ml |
| 1.0 M Phosphate buffer, pH 7.5 | 0.5 ml |
| Anhydrous D-glucose | 1.44 g. |
| Distilled water | To make up a total volume of 7.5 ml. |

The enzyme preparation to be assayed is first diluted to contain from 1 to 6 IGIU/ml.

An enzymatic isomerization is conducted by adding 1 ml of the enzyme preparation to 3 ml of the stock solution, and incubating for 30 minutes at 60° C. At the end of the incubation period, a 1 ml aliquot is taken and quenched in a 9 ml volume of 0.5 N perchloric acid. The quenched aliquot is then diluted to a total volume of 250 ml. As a control, for comparative purposes, a glucose blank is also run by substituting 1 ml of water for 1 ml of the enzyme preparation in solution form, at the beginning of the incubation period. The ketose is then determined by a cysteine-sulfuric acid method. For the purposes of this assay, one IGIU is defined as the amount of enzyme activity that is required to produce one micromole of fructose per minute under the isomerization conditions described above.

Adsorption of the polysaccharide in, for example, a column should be carried out by passing the enzyme preparation through the column at a flow rate of BVH 0.5 to BVH 10, preferably at BVH 1.0, or by circulating the preparation through the column for a period of 3 to 24 hours, preferably from 10 to 15 hours. BVH, also referred to as SV or "space velocity", is the column flow rate in bed volumes per hour.

In carrying out the adsorption by a batch system inside a vessel, the enzyme preparation is generally contacted with the above-mentioned adsorbent, while stirring, for a period ranging from 30 minutes to 24 hours, preferably for 2 to 5 hours. In this way, the polysaccharide is adsorbed and separated from the enzyme preparation.

At the time of adsorption of the polysaccharide, the pH of the enzyme preparation should be within the range of 4 and 11, and preferably in the vicinity of 5. In addition, its temperature should be in the range of 4° to 60° C., with room temperature being especially desirable.

In practicing the previously-mentioned method of employing an organic solvent to separate polysaccharide, the solvent can be any which is capable of precipitating the enzyme while causing little or no precipitation of co-existing polysaccharides. Representative solvents are methanol, ethanol, propanol, isopropanol, t-butanol, acetone, p-dioxane or mixtures thereof.

Organic solvents are added to the preparation in an amount sufficient to bring about the precipitation of the enzyme while causing substantially no precipitation of the polysaccharide. For example, when using isopropanol, it may be added in an amount sufficient to achieve a concentration of 30 to 38% by vol., preferably about 36% by vol. Acetone should be added to give a concentration of 27 to 36% by vol., preferably between 30 and 33% by vol.; ethanol, 36 to 45%, preferably between 38 and 42% by vol.; methanol, 44 to 55%; propanol, 30 to 38% by vol.; t-butanol, 28 to 36% by vol.; and p-dioxane, 28 to 36% by vol.

To use these organic solvents, the enzyme preparation is generally first adjusted to a pH of between 5 and 8, preferably about pH 7, and the organic solvent (pre-cooled to a temperature of 10° C. to −20° C.) is then added while stirring gently until the desired concentration is reached. After the appropriate concentration of solvent is attained, the stirring is continued for another 30 minutes to 2 hours. Following that, the precipitated enzyme is collected, either by centrifugal separation or by decantation or the like, and this is then dissolved in a solvent such as water.

Salts which can be added to the enzyme solutions to bring about selective precipitation include ammonium sulfate, sodium sulfate, and magnesium sulfate. However, it is equally possible to employ any other salt which is capable of performing this function.

These salts should be added to the preparation to obtain a concentration such that they bring about the desired, selective precipitation of enzyme. In this case of ammonium sulfate, for example, the addition should be carried out to give a level of 45% or higher, preferably 50% to 60% of saturation by total weight.

The salt is preferably added to an enzyme preparation having a pH of between 5 and 8, preferably about pH 7, while stirring gently. After the appropriate concentration of the salt is attained, the stirring is continued for a further 30 minutes to 2 hours. Following that, the precipitated enzyme is collected, either by centrifugal separation or by decantation, and this is then redissolved.

An enzyme solution, which was obtained in the above-mentioned way and which had been essentially completely freed of adsorption-inhibiting polysaccharide, may then be contacted with an adsorptive carrier to immobilize enzyme thereon.

Suitable adsorptive carriers include such known materials as ion exchange resins, DEAE-cellulose, basic magnesium carbonate, colloidal silica, active carbon, and controlled Pore Alumina.

Exemplary adsorptive ion exchange resins are Amberlite IRA-904, Amberlite IRA-938, Amberlite IRA-93, (the foregoing are all brand names of products of Tokyo Yuki Kagaku Kogyo Co., Ltd.), Diaion PA-302, Diaion PA-304, Diaion PA-308, Diaion WA-20 (the foregoing are all brand names of products of Mitsubishi Kasei Kogyo Co., Ltd.), Duolite A-2, Duolite A-7, Duolite S-3, Duolite ES-561 and Duolite ES-562 (the foregoing are all brand names of products of Diamond Shamrock Chemical Co., Ltd., of the U.S.A.).

In the case where the carrier is an ion exchange resin, it is possible for the exchange group to be any of OH-form, Cl-form, $SO_4$-form, etc., but it is most desirable to employ the Cl-form derived by regeneration with NaCl or HCl.

DEAE-cellulose carriers useful to immobilize enzyme include such known materials as Selectacel-20 (the brand name of a product of Brown Co., of West Germany); as the colloidal silica it is possible to mention LUDOX HS-30, LUDOX HS-40, LUDOX AM, LUDOX TM (all of the foregoing are brand names of products of DuPont Co., Ltd., of the U.S.A.). Snowtex 20, Snowtex 30, Snowtex N (all of the foregoing are brand names of products of Nissan Kagaku Co., Ltd.). An exemplary controlled Pore Alumina is the product of Corning Co., Ltd., of the U.S.A., and as the active carbon it is possible to mention Darco S-51 and Darco G-60 (both brand names of products of Atlas Co., Ltd., of Denmark).

In carrying out the adsorption or immobilization of enzyme by contacting an enzyme solution which contains substantially no polysaccharide with one of the above-mentioned carriers, the solution—either as is or after it has been adjusted to a desired concentration (for example, a glucose isomerase concentration of 50 U/ml to 1,000 U/ml, preferably about 300 U/ml) by concentration or dilution—is contacted with the carrier, either in a column or in some other appropriate vessel.

At the time of immobilization, it is desirable for the pH of enzyme solution to be in the range of 4 to 11, especially in the vicinity of pH 7 to 8. In addition, the temperature is desirably between 4° C. and 60° C., especially about room temperature.

When immobilization is performed in a column, the enzyme solution should be introduced to said column at a flow-rate of BVH 0.5 to BVH 10, preferably at BVH 1.0. Alternatively, the adsorption can be carried out by circulation through the column for a period of 3 hours to 24 hours, preferably for a period of 10 hours or 15 hours.

When immobilization is performed in a suitable vessel for batch-type adsorption, the enzyme solution should be contacted with the carrier for a period of 30 minutes to 24 hours, preferably for a period between 2 hours and 5 hours, while stirring the mixture.

In the section which follows, some examples are presented in order to demonstrate the inhibitory effect of saccharides on the adsorption of the enzyme onto a carrier.

EXPERIMENTAL EXAMPLE 1

*Streptomyces olivochromogenes* (FERM 1640, ATCC 21114), was shake-cultured in liquid culture medium at 30° C. for about 50 hours. The cultured material was then centrifuged for 20 minutes at 10,000 rpm to collect the cells. The wet cells were weighed and then suspended in ion exchange water (3 volumes) containing 10 mM $MgCl_2$. Next 0.02% of lysozyme (a product of Behringer-Manheim Co.) and 1% toluene by weight of wet cells were added and lysis was carried out for 24 hours at 30° C. under gentle stirring. The resulting lysate was then centrifuged for 20 minutes at 10,000 rpm and the cellular debris eliminated.

An equal volume of isopropyl alcohol was next added to the supernatant while it was being gently stirred. This mixed solution was further centrifuged and the precipitate collected. The precipitate was then dissolved in a small amount of deionized water containing 10 mM $MgCl_2$. The performance of the above series of operations resulted in a recovery of over 70% of the initial, intracellular glucose isomerase in a soluble form.

The same microorganism strain was employed and the preceding operations were repeated 19 times so that 19 different glucose isomerase solutions were prepared. These 19 glucose isomerase solutions were then employed in the experiment described below.

Nineteen columns having dimensions of 1.6×20 cm were each packed with 10 ml of Amberlite IRA-904 (the brand name of a product of Tokyo Yuki Kagaku Kogyo Co., Ltd.), a strongly basic ion exchange resin. The columns were then washed with deionized water. The previously-mentioned 19 glucose isomerase solutions were diluted so that their concentrations were 500 U/ml and then 10 ml was supplied to each of the prepared columns at a flow-rate of BVH 1.0. These glucose isomerase solutions were circulated in their respective columns at the same flow-rate for one night to adsorb and immobilize the enzyme.

Each of these columns was then washed with 100 ml of deionized water to remove the unadsorbed matter from the columns, and the amount of glucose isomerase activity in the wash solutions was determined. The equations given below were then used to calculate the amount of glucose isomerase activity adsorbed per milliliter of the ion exchange resin, and the adsorption efficiency for each of the 19 columns. The total activity of the glucose isomerase supplied to the column is designated as (A), the glucose isomerase activity found in the wash solution as (B), and the volume (ml) of the ion exchange resin as (C).

$$\text{GI activity adsorbed/ml } IER = \frac{A-B}{C}$$

$$\text{Adsorption Efficiency} = \frac{A-B}{A}$$

Next, 5 ml aliquots of each of the above-mentioned 19 glucose isomerases were dialyzed for one night against deionized water containing 10 mM $MgCl_2$ and 1 mM $CoCl_2$. The dialysis removed the propanol and low molecular weight saccharides contained in the glucose isomerase solution, but the non-dialyzable polysaccharides were retained. The glucose isomerase activities of these dialyzed glucose isomerase solutions were determined, and their contents of polysaccharide were measured by the phenol-sulfuric acid method. The amount of polysaccharide per unit of glucose isomerase was also calculated.

The 19 glucose isomerase solutions were placed in the order of the highest adsorption efficiency for Amberlite IRA-904. They are listed in the accompanying Table 1 as glucose isomerase solutions A, B, C, - - - Q, R, and S, together with the results of the determinations described above.

The results presented in Table 1, show that the presence of a fair amount of high molecular weight polysaccharide (which is not eliminated even by overnight dialysis) interferes with the adsorption of the glucose isomerase by the ion exchange resin.

TABLE 1

| Glucose Isomerase Solution | Adsorbed Amount (U/ml-resin) | Adsorption Efficiency (%) | Polysaccharide Amount ($\gamma$/U) |
| --- | --- | --- | --- |
| A | 381 | 76.2 | 4.7 |
| B | 371 | 74.2 | 5.5 |
| C | 342 | 68.4 | 10.9 |
| D | 341 | 68.2 | 8.2 |
| E | 326 | 65.2 | 9.1 |
| F | 313 | 62.6 | 8.3 |
| G | 308 | 61.6 | 10.4 |
| H | 305 | 61.0 | 12.2 |
| I | 286 | 57.2 | 12.1 |
| J | 256 | 51.2 | 14.4 |
| K | 255 | 51.0 | 14.5 |
| L | 248 | 49.6 | 12.5 |
| M | 247 | 49.4 | 15.1 |
| N | 241 | 48.2 | 19.4 |
| O | 235 | 47.0 | 16.0 |
| P | 227 | 45.4 | 16.7 |
| Q | 211 | 42.2 | 17.9 |
| R | 200 | 40.0 | 16.3 |
| S | 159 | 31.8 | 19.6 |

EXPERIMENTAL EXAMPLE 2

Glucose isomerase solution S, the solution which showed the poorest glucose isomerase binding to Amberlite IRA-904 of all of the 19 glucose isomerase preparations of Experimental Example 1, was employed in the following experiments.

Twenty milliliters of solution S (containing 40,000 units of glucose isomerase) was dialyzed overnight against a 0.05 M tris-HCl buffer solution (pH 7.0; containing 10 mM $MgCl_2$ and 1 mM $CoCl_2$). This dialyzed glucose isomerase solution was then supplied to a DEAE-cellulose column (having dimensions of 2.2×50 cm, and containing 150 ml of DEAE-cellulose). The column had previously been equilibrated with the same buffer, at a flow-rate of 38.5 ml/hr. The glucose isomerase and the polysaccharides were then adsorbed onto the carrier.

Figure 1:
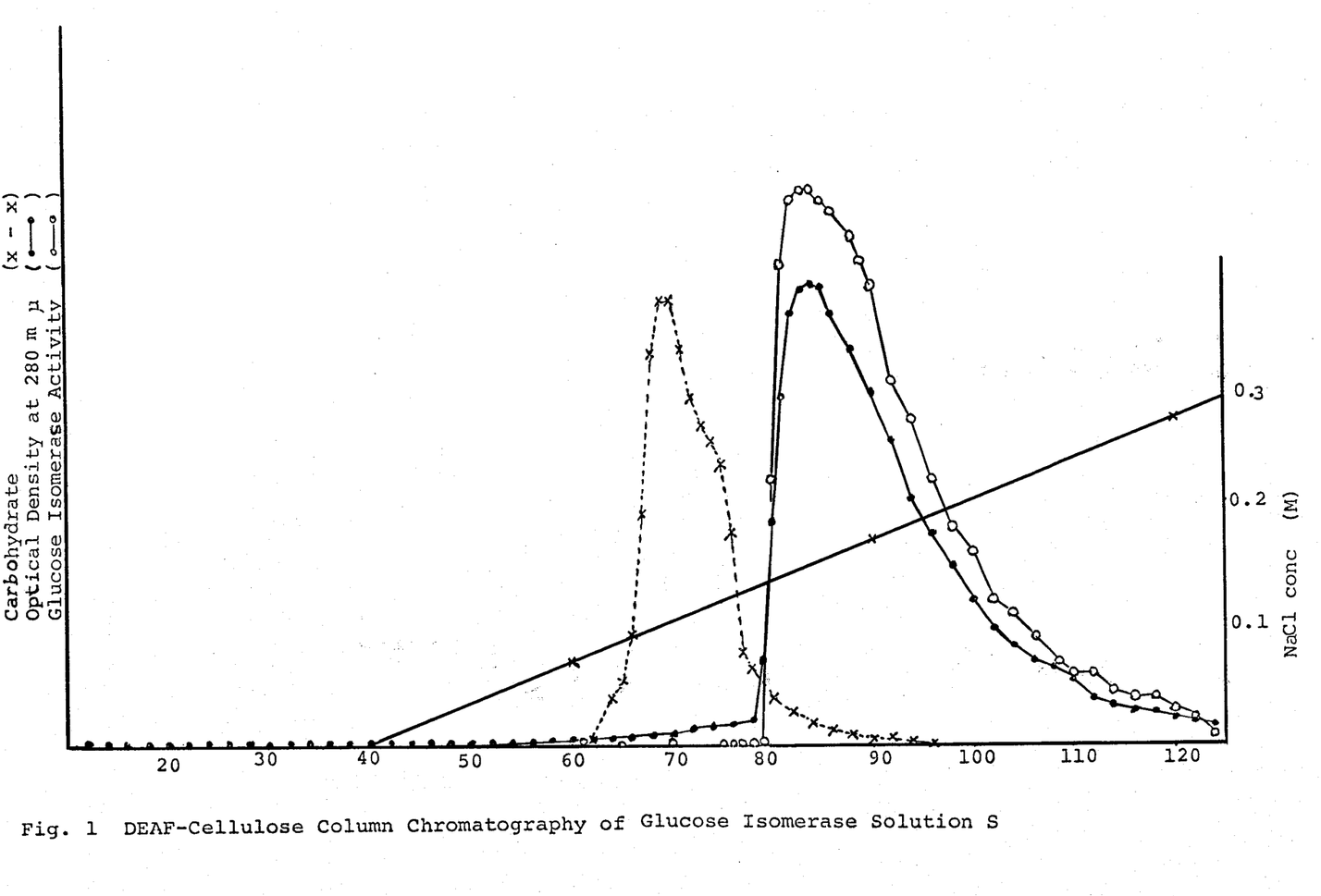
The FIGURE illustrates the elution pattern for glucose isomerase and polysaccharide as described in Experimental Example 2.

Elution was carried out by the concentration gradient method using an NaCl concentration range of from 0 to 0.5 M. The eluate was collected in 7 ml portions with a fraction collector. Each fraction was analyzed for its glucose isomerase activity, its absorbance at 280 m$\mu$, and its polysaccharide content. FIG. 1 illustrates the elution patterns for the glucose isomerase (i.e. protein) and polysaccharide.

As is clear from FIG. 1, the glucose isomerase was eluted at an NaCl concentration of 0.15 M, while the polysaccharide eluted at an NaCl concentration of 0.1 M. This result indicates that the glucose isomerase and the polysaccharide which coexist in the glucose isomerase solution were successfully separated. The glucose isomerase obtained in this way was concentrated using 60% isopropanol, while the polysaccharide was concentrated in an evaporator. This polysaccharide separated from the glucose isomerase solution S and purified was found to have an average molecular weight of about 34,000.

The same experimental procedures were applied to glucose isomerase solutions H and B from Experimental Example 1, and similar results were obtained.

EXPERIMENTAL EXAMPLE 3

The procedure described in Experimental Example 2 was followed and the polysaccharide was separated and concentrated from glucose isomerase solution S, and the purified glucose isomerase preparation was also prepared. These two materials, plus solution S, were then employed for the following experiments.

Three columns having dimensions of 1.6×20 cm were each filled with 10 ml of Amberlite IRA-904 resin and then washed well with deionized water. Solution S was next supplied to column 1, the purified glucose isomerase preparation to column 2, and column 3 received a solution prepared by readdition of polysaccharide to the purified glucose isomerase preparation.

In each case, the glucose isomerase concentration was diluted to about 500 U/ml and then the solutions were supplied to the columns at a flow-rate of BVH 1.0. The solutions were circulated through the columns overnight at the same flow-rate, in order to effect adsorbtion by the resin.

The enzyme solutions supplied to each of these three columns contained 5,000 units of glucose isomerase activity, and there were 88 mg of the polysaccharide contained in each of the enzyme solutions supplied to columns 1 and 3. Following the completion of the adsorption operations, each of the columns was washed with 100 ml of deionized water to remove unadsorbed matter from the resin beds. The amounts of glucose isomerase and polysaccharide contained in each wash solution were determined, and the adsorption extents for the glucose isomerase and polysaccharide to the Amberlite IRA-904 resins were calculated. The results were as presented in the following table.

TABLE 2

| Column | Sample | Adsorption Efficiency (%) | |
| --- | --- | --- | --- |
| | | Glucose Isomerase | Poly-saccharide |
| 1 | GI Solution S | 28.3 | 76.0 |
| 2 | Purified GI Solution | 99.0 | — |
| 3 | Purified GI Solution With Polysaccharide Added | 26.4 | 81.4 |

Next, the procedure described in Experimental Example 2 was followed and the purified glucose isomerases and polysaccharides were prepared from glucose isomerase solutions H and B. These materials were then employed in the manner just described. The results for these experiments are presented in the following two tables.

TABLE 3

| Column | Sample | Adsorption Efficiency (%) | |
|---|---|---|---|
| | | Glucose Isomerase | Poly-saccharide |
| 1 | GI Solution H | 61.0 | 80.6 |
| 2 | Purified GI Solution | 99.3 | — |
| 3 | Purified GI Solution With Polysaccharide Added | 25.3 | 81.4 |

TABLE 4

| Column | Sample | Adsorption Efficiency (%) | |
|---|---|---|---|
| | | Glucose Isomerase | Poly-saccharide |
| 1 | GI Solution B | 74.2 | 88.5 |
| 2 | Purified GI Solution | 99.1 | — |
| 3 | Purified GI Solution With Polysaccharide Added | 27.6 | 76.1 |

The data shows that the polysaccharide in the glucose isomerase solutions is adsorbed by glucose isomerase-adsorbing carriers, for example ion exchange resins, more selectively than the glucose isomerase itself. It thus exerts a striking effect of inhibition on the adsorption of the glucose isomerase. It is also clear that the elimination, or the reduction in the amount, of the polysaccharide in the glucose isomerase solutions results in an increased adsorption for the glucose isomerase.

EXPERIMENTAL EXAMPLE 4

Glucose isomerase solution S prepared in Experimental Example 1 was dialyzed overnight at 4° C. against deionized water containing 10 mM $MgCl_2$ and 1 mM $CoCl_2$ (hereinafter referred to simply as 'deionized water'). The external dialysis solution of deionized water was frequently changed during the course of the dialysis.

The dialyzed solution was then divided into 16 ml aliquots (each containing 9,683 units of glucose isomerase and 189.79 mg of polysaccharide) and placed in each of ten 50-ml beakers. Cold isopropanol was slowly added with stirring to each beaker in respective volumes of 6, 7, - - -, 14 and 15 ml. The stirring was continued for 30 minutes at 4° C. Each mixture was then transferred to a centrifuge tube and centrifugation was carried out for 15 minutes at 15,000 rpm.

The supernatant was removed by decantation and discarded, and the precipitate was dissolved in about 30 ml of deionized water. Each of the 10 solutions obtained in this way was then placed in a 50-ml volumetric flask and filled to 50 ml in volume with deionized water. The total glucose isomerase activities and the polysaccharide contents were determined for each of these solutions.

The total glucose isomerase activity contained in the original 16 ml of glucose isomerase solution employed was designated as $E_1$, and the polysaccharide content therein was designated as $P_1$. The amount of glucose isomerase activity contained in the recovered material was termed $E_2$, and the amount of polysaccharide contained therein was termed $P_2$. These values were substituted in the following equations and the recovery percentages for glucose isomerase and polysaccharide were calculated for each of the 10 isopropanol-treated preparations. The amounts of polysaccharide per unit of glucose isomerase was also calculated for each of the obtained solutions.

GI Recovery $= E_2/E_1 \times 100$

Polysaccharide Recovery $= P_1/P_2 \times 100$

Polysacch./U of GI $(\gamma/U) = P_2/E_2$

The results of the calculations using these equations are presented in the accompanying Table 5.

TABLE 5

Effect of Isopropanol Concentration on Separation of Glucose Isomerase Enzyme and Polysaccharide

| Iso-propanol Conc. (vol-%) | Recovered Enzyme | | Recovered Polysaccharide | | Polysacch/U of ($\gamma$/U) |
|---|---|---|---|---|---|
| | Activity (U) | (%) | Amount (mg) | (%) | |
| 27.3 | 397.2 | 4.10 | 9.41 | 4.96 | 23.69 |
| 30.4 | 6826 | 70.49 | 31.81 | 16.76 | 4.66 |
| 33.3 | 8831 | 91.20 | 30.76 | 16.21 | 3.48 |
| 36.0 | 9167 | 94.67 | 53.58 | 28.23 | 5.84 |
| 38.5 | 9176 | 94.76 | 107.16 | 56.46 | 11.68 |
| 40.7 | 9459 | 97.69 | 143.63 | 75.68 | 15.18 |
| 42.9 | 9613 | 99.28 | 148.42 | 78.20 | 15.44 |
| 44.8 | 9600 | 99.14 | 157.98 | 83.24 | 16.46 |
| 46.7 | 9600 | 99.14 | 165.97 | 87.45 | 17.29 |
| 48.4 | 9344 | 96.50 | 153.20 | 80.72 | 16.40 |

Table 5 shows that the polysaccharide is barely precipitated, as long as the concentration of the isopropanol is 36.0% by vol. or less, but that it is progressively precipitated with enzyme as the isopropanol concentration becomes higher. On the other hand, it is clear that the recovery rate of the glucose isomerase is quite high even at an isopropanol concentration of 33% by vol. By employing isopropanol in a concentration of 30 to 38% by vol., preferably about 36% by vol., it is therefore possible to preferentially precipitate the glucose isomerase with almost no drop in its recovery. At the same time, polysaccharide which inhibits the adsorption of the glucose isomerase to resin carriers is left behind in the liquid phase.

Next, 10 ml of wet Amberlite IRA-904 resin was packed in each of 9 columns having dimensions of 1.6×20 cm, and these were washed well with deionized water. The glucose isomerase solution S was handled in the same way as before and aliquots of it were treated with 9 different concentrations of isopropanol (at 30.4% by vol. and above). The glucose isomerase precipitates were obtained and dissolved in deionized water. The enzyme preparations thus prepared were adjusted to contain 3,000 units of glucose isomerase (in enzyme solution volumes of 15.6 to 22 ml) and were then circulated through the above-mentioned columns overnight at a flow-rate of BVH 1 and room temperature.

Following completion of the circulation and adsorption, each of the columns was washed with 50 ml of deionized water to remove unadsorbed matter in the resin bed. The wash solutions were analyzed for their contents of glucose isomerase activity. The results were as shown in Table 6 below.

TABLE 6

| | Isopropanol Concentration (% by Vol.) | | | | | | | | |
|---|---|---|---|---|---|---|---|---|---|
| | 30.4 | 33.3 | 36.0 | 38.5 | 40.7 | 42.9 | 44.8 | 46.7 | 48.4 |
| Adsorbed GI per 1ml resin (U/ml) | 300 | 300 | 300 | 285 | 256 | 250 | 241 | 217 | 198 |
| Adsorption Efficiency (%) | 100 | 100 | 100 | 95.0 | 85.3 | 83.3 | 80.3 | 72.3 | 66.0 |

It is evident from the results presented in Table 6 that concentrations of 30 to 38% by vol. are the most desirable when employing isopropanol to bring about the preferential precipitation of glucose isomerase while leaving the polysaccharide behind in the liquid phase.

EXPERIMENTAL EXAMPLE 5

The dialyzed glucose isomerase solution prepared in Experimental Example 4 was employed, and 16 ml (containing 9,683 U of glucose isomerase and 189.79 mg of polysaccharide) aliquots of the enzyme solution were placed in seven 50-ml beakers. Then, while the solutions were being stirred, cold acetone was slowly added in volumes of 6, 7, - - -, 11 and 12 ml to the beakers. The stirring was continued for 30 minutes at 4° C. The mixtures were each transferred to centrifuge tubes, and centrifugation was carried out for 15 minutes at 15,000 rpm.

The supernatants were decanted and discarded, and the precipitates were each dissolved in about 30 ml of deionized water. These solutions were then transferred to 50-ml volumetric flasks and their volumes were made up to 50 ml with deionized water. Each of these enzymes solutions was then analyzed for its total glucose isomerase activity content and its total polysaccharide content. The results of this experiment are presented in Table 7.

It is clear that the polysaccharide contained in the glucose isomerase solution is barely precipitated so long as the concentration of the acetone is 33.3% by vol. or less. It is precipitated and recovered at high rates at acetone concentrations of 36% by vol. and above. The glucose isomerase, on the other hand, is recovered at a high rate even when the acetone concentration is 30.4% by vol.

TABLE 7

Effect of Acetone Concentration on Separation of Glucose Isomerase and Polysaccharide

| Acetone Conc. (% by Vol.) | Recovered Enzyme Activity (U) | Rate (%) | Recovered Polysaccharide Amount (mg) | Rate (%) | Polysacch./ U of GI (γ/U) |
|---|---|---|---|---|---|
| 27.3 | 7704 | 79.56 | 13.17 | 6.94 | 1.71 |
| 30.4 | 9385 | 96.92 | 17.29 | 9.11 | 1.84 |
| 33.3 | 9410 | 97.18 | 42.38 | 22.33 | 4.50 |
| 36.0 | 9260 | 95.63 | 158.42 | 83.47 | 17.11 |
| 38.5 | 9285 | 95.89 | 180.64 | 95.18 | 19.46 |
| 40.7 | 9272 | 95.76 | 189.28 | 99.73 | 20.41 |
| 42.9 | 8833 | 91.22 | 181.06 | 95.40 | 20.50 |

By employing acetone in a concentration of 30 to 33% by vol., it is therefore possible to preferentially precipitate the glucose isomerase with almost no drop in its extent of recovery. At the same time, polysaccharide which inhibits the adsorption of the glucose isomerase to resin carriers is left behind in the liquid phase.

Next, 10 ml of wet Amberlite IRA-904 resin was packed in each of 7 columns having dimensions of 1.6×20 cm. These were washed well with deionized water. The glucose isomerase solution S was handled in the same way as before and aliquots of it were treated with 7 different concentrations of acetone. The glucose isomerase precipitates were obtained and dissolved in deionized water. The enzyme solutions thus prepared were adjusted to contain 3,000 units of glucose isomerase activity (in enzyme solution volumes of 16 to 19 ml) and were then circulated through the above-mentioned columns overnight at a flow-rate of SV 1 and room temperature.

Following completion of the circulation and adsorption, each of the columns was washed with 50 ml of deionized water to remove unadsorbed matter in the resin bed. The wash solutions were analyzed for their contents of glucose isomerase activity. The results were as shown in Table 8 below.

TABLE 8

| | Acetone Concentration (% by Vol.) | | | | | | |
|---|---|---|---|---|---|---|---|
| | 27.3 | 30.4 | 33.3 | 36.0 | 38.5 | 40.7 | 42.9 |
| Adsorbed GI/ml resin (U/ml) | 300 | 300 | 300 | 219 | 158 | 149 | 151 |
| Adsorption Efficiency (%) | 100 | 100 | 100 | 73 | 52.7 | 49.7 | 50.3 |

It is evident from the results presented in Table 8 that concentrations of 27 to 36% by vol. are the most desirable when employing acetone to bring about the selective precipitation of glucose isomerase.

EXPERIMENTAL EXAMPLE 6

The dialyzed glucose isomerase solution prepared in Experimental Example 4, was employed and 11 ml (containing 6,657 U of glucose isomerase and 130.48 mg of polysaccharide) aliquots of this enzyme solution were placed in six 50-ml beakers. Then, while the solutions were being gently stirred, cold ethanol was slowly added in volumes of 6, 7, 8, 9, 10 and 11 ml to the beakers. The stirring was continued for 30 minutes at 4° C. Then the mixtures were each transferred to centrifuge tubes. Centrifugation of these was carried out for 15 minutes at 15,000 rpm.

The supernatants were decanted and discarded, and the precipitates were each dissolved in about 15 ml of deionized water. These solutions were then transferred to 25-ml volumetric flasks and their volumes were made up to 25 ml with deionized water. Each of these enzyme solutions was then analyzed for its total glucose isomerase activity content and its total polysaccharide content. The results were as presented in Table 9.

TABLE 9

Effect of Ethanol Concentration on Separation of Glucose Isomerase and Polysaccharide

| Ethanol Conc. (% by Vol.) | Recovered Enzyme Activity (U) | (%) | Recovered Polysaccharide Amount (mg) | (%) | Polysacch. γ/U of GI |
|---|---|---|---|---|---|
| 35.3 | 4505 | 67.68 | 4.67 | 3.58 | 1.04 |
| 38.9 | 6657 | 100 | 14.85 | 11.38 | 2.23 |

TABLE 9-continued
Effect of Ethanol Concentration on Separation of Glucose Isomerase and Polysaccharide

| Ethanol Conc. (% by Vol.) | Recovered Enzyme Activity (U) | (%) | Recovered Polysaccharide Amount (mg) | (%) | Polysacch. γ/U of GI |
|---|---|---|---|---|---|
| 42.1 | 6624 | 99.50 | 40.31 | 30.89 | 6.09 |
| 45.0 | 6624 | 99.50 | 80.64 | 61.80 | 12.17 |
| 47.6 | 6421 | 96.46 | 95.60 | 73.27 | 14.89 |
| 50.0 | 6556 | 98.48 | 107.79 | 82.61 | 16.44 |

It is clear from the results presented in Table 9 that the polysaccharide contained in the glucose isomerase solution is barely precipitated and recovered as long as the concentration of the ethanol is 42.1% by vol. or less. It is precipitated and recovered at progressively higher ethanol concentrations of 45.0% by vol. and above. The glucose isomerase, on the other hand, is subject to complete recovery at an ethanol concentration of 38.9% by vol.

By employing ethanol in a concentration of 38 to 42% by vol., it is therefore possible to selectively precipitate the glucose isomerase with almost no drop in its recovery rate. At the same time, polysaccharide which inhibits the adsorption of the glucose isomerase to resin carriers is left behind in the liquid phase.

Next, 10 ml of wet Amberlite IRA-904 resin was packed in each of six columns having dimensions of 1.6×20 cm, and these were washed well with deionized water. The glucose isomerase solution S was handled in the same way as before and aliquots of it were treated with six different concentrations of ethanol. The glucose isomerase precipitates were obtained and dissolved in deionized water. The enzyme solutions thus prepared were adjusted to contain 3,000 units of glucose isomerase activity (in enzyme solution volumes of 11.3 to 16.7 ml) and were then circulated through the above-mentioned columns overnight at a flow rate of BVH 1 and room temperature.

Following completion of the circulation and adsorption, each of the columns was washed with 50 ml of deionized water to remove unadsorbed matter from the resin bed. The wash solutions were analyzed for their contents of glucose isomerase activity. The results were as shown in Table 10 below.

TABLE 10

|  | Ethanol Concentration (% by Vol.) | | | | | |
|---|---|---|---|---|---|---|
|  | 35.3 | 38.9 | 42.1 | 45.0 | 47.6 | 50.0 |
| Adsorbed GI U/ml of resin | 300 | 300 | 300 | 293 | 247 | 233 |
| Adsorption Efficiency (%) | 100 | 100 | 100 | 97.7 | 82.3 | 77.7 |

It is evident from the results presented in Table 10 that concentrations of 36 to 45% by vol. are the most desirable when employing ethanol to bring about the selective precipitation of glucose isomerase.

EXPERIMENTAL EXAMPLE 7

The dialysis treatment was carried out as described in Experimental Example 4 and 16 ml (containing 9,683 U of glucose isomerase and 189.79 mg of polysaccharide) aliquots of the obtained enzyme solution were placed in each of six 50-ml beakers. Then, while the solutions were being gently stirred at 4° C., ammonium sulfate was added to give respective degrees of saturation of 45% 50%, 55%, 60%, 65%, and 70%. The stirring was continued for another 30 minutes. Then the mixtures were each transferred to centrifuge tubes. Centrifugation of these was carried out for 15 minutes at 15,000 rpm.

The supernatants were decanted and discarded, and each of the precipitates was separately dissolved in about 30 ml of deionized water. These solutions were then transferred to 50-ml volumetric flasks and their volumes were made up to 50 ml with deionized water. Each of these enzyme solutions was then analyzed for its total glucose isomerase activity content and its polysaccharide content. The results were as presented in Table 11 below.

It is clear from the results presented in Table 11 that the polysaccharide contained in the glucose isomerase solution is barely precipitated at ammonium sulfate degrees of saturation of 45% to 70%, or over the full range of saturation degrees tested here. The glucose isomerase, on the other hand, is nearly completely precipitated and recovered at ammonium sulfate saturation degrees of 50% or more.

By employing ammonium sulfate, it is possible to selectively precipitate glucose isomerase from a polysaccharide-containing glucose isomerase solution.

TABLE 11
Effect of Ammonium Sulfate Concentration on Separation of Glucose Isomerase and Polysaccharide

| Ammonium Sulfate Conc. (% saturated) | Recovered Enzyme Activity (U) | (%) | Recovered Polysaccharide Amount (mg) | (%) | Polysacch. γ/U of GI |
|---|---|---|---|---|---|
| 45 | 4499 | 46.46 | 7.91 | 4.17 | 1.76 |
| 50 | 8264 | 85.35 | 16.76 | 8.83 | 2.03 |
| 55 | 9096 | 93.94 | 15.18 | 8.00 | 1.67 |
| 60 | 9585 | 98.99 | 16.76 | 8.83 | 1.75 |
| 65 | 9683 | 100 | 22.77 | 12.00 | 2.35 |
| 70 | 9683 | 100 | 23.40 | 12.33 | 2.42 |

Next, 10 ml of wet Amberlite IRA-904 resin was packed in each of six columns having dimensions of 1.6×20 cm, and these were washed well with deionized water. The glucose isomerase solution S was handled in the same way as before and aliquots of it were treated with six different concentrations of ammonium sulfate. The glucose isomerase precipitates were obtained and dissolved in deionized water. The enzyme solutions thus prepared were adjusted to contain 3,000 units of glucose isomerase activity (in enzyme solution volumes of 15.5 to 33.3 ml) and were then circulated through the above-mentioned columns overnight at a flow-rate of BVH 1 and room temperature.

Following completion of the circulation and adsorption, each of the columns was washed with 50 ml of deionized water to remove unadsorbed matter from the resin bed. The wash solutions were analyzed for their contents of glucose isomerase activity. The results were as shown in Table 12.

It is evident from the results presented in Table 12 that concentrations of ammonium sulfate giving degrees of saturation of 45% and higher are the most desirable when employing ammonium sulfate to bring about the selective precipitation of glucose isomerase.

TABLE 12

|  | Ammonium Sulfate Concentration (% Saturation) | | | | | |
|---|---|---|---|---|---|---|
|  | 45 | 50 | 55 | 60 | 65 | 70 |
| Adsorbed GI U/ml | 300 | 300 | 300 | 300 | 300 | 300 |

TABLE 12-continued

| | Ammonium Sulfate Concentration (% Saturation) | | | | | |
|---|---|---|---|---|---|---|
| | 45 | 50 | 55 | 60 | 65 | 70 |
| of resin Adsorption Efficiency (%) | 100 | 100 | 100 | 100 | 100 | 100 |

The glucose isomerase-containing solution, which was obtained in the above-mentioned way and which had been completely or nearly completely freed of polysaccharide, was then contacted with a glucose isomerase-adsorbing carrier and the glucose isomerase was adsorbed thereon.

Next, the present invention will be explained in a more detailed fashion by the presentation of applied examples and also comparative examples. The present invention is however, in no way limited by those examples.

EXAMPLE 1

Ten milliliters of moist Lewatit M-500 (brand name of a product of Bayer Co., Ltd., of West Germany), a strongly-basic anion exchange resin (type-I), was packed in a column having dimensions of 1.6×20 cm. This resin column was then treated with 50 ml of a 2 M NaCl solution at BVH 1, before thorough washing with water. Next, the glucose isomerase solution S prepared as described in Experimental Example 1 was employed and 3 ml (containing 5,000 U of glucose isomerase and 98 mg of polysaccharide out of a total saccharide content of 112 mg) was circulated through the above-mentioned column overnight at a flow-rate of BVH 1 and room temperature.

This column was then washed with 20 ml of deionized water to remove unadsorbed matter from the resin bed. The wash solution was later analyzed for its contents of glucose isomerase activity and total saccharides, and the adsorption efficiencies for the glucose isomerase and total saccharides were calculated. The results indicated that the glucose isomerase was barely adsorbed by the Lewatit M-500, whereas 80.1% of the total saccharides was adsorbed.

Next, 10 ml of moist Amberlite IRA-904 (brand name of a product of Tokyo Yuki Kagaku Kogyo Co., Ltd.) was packed in a column having dimensions of 1.6×20 cm, and this column was thoroughly washed with deionized water. Then the glucose isomerase solution which was obtained by eliminating most of the polysaccharide from glucose isomerase solution S by treating it as previously described on a Lewatit M-500 column was employed in a volume of 15 ml (containing 3,000 U of glucose isomerase) and supplied to said Amberlite IRA-904 column and circulated through it overnight at a flow-rate of SV 1 and room temperature.

The column was then washed with 50 ml of deionized water to remove unadsorbed matter from the resin bed, and the wash solution was analyzed for its glucose isomerase content. The results confirmed that 99.4% of the supplied glucose isomerase was adsorbed by the Amberlite IRA-904 resin. This Amberlite IRA-904 with glucose isomerase adsorbed to it can be employed as an immobilized glucose isomerase.

EXAMPLE 2

Ten milliliters of moist Lewatit M-504 (brand name of a product of Bayer Co., Ltd., of West Germany), a strongly-basic anion exchange resin type-I, was packed in a 1.6×20 cm column. This column was then treated with 50 ml of a 2 M NaCl solution at BVH 1, followed by thorough washing with water. Glucose isomerase solution S prepared as described in Experimental Example 1 was employed and 3 ml (containing 5,000 U of glucose isomerase and 98 mg of polysaccharide out of a total saccharide content of 112 mg) of this was circulated through the above-mentioned column overnight at a flow-rate of SV 1 and room temperature.

This column was then washed with 20 ml of deionized water to remove unadsorbed matter from the resin bed. The wash solution was later analyzed for its contents of glucose isomerase activity and total saccharides, and the adsorption efficiencies for the glucose isomerase and total carbohydrates were calculated. The results indicated that the glucose isomerase was barely adsorbed by the Lewatit M-504, whereas 81.0% of the total saccharides was adsorbed.

Next, 10 ml of moist Amberlite IRA-904 was packed in a 1.6×20 cm column, and this column was then washed thoroughly with deionized water. Then the glucose isomerase solution obtained by eliminating most of the polysaccharide from glucose isomerase solution S by treating it as previously described on a Lewatit M-504 column was employed in a volume of 15 ml (containing 3,000 U of glucose isomerase) and supplied to the Amberlite IRA-904 column and circulated through it overnight at a flow-rate of BVH 1 and room temperature.

The column was then washed with 50 ml of deionized water to wash out the unadsorbed matter from the resin bed, and the wash solution was analyzed for its glucose isomerase activity. The results confirmed that 99.5% of the supplied glucose isomerase was adsorbed by the Amberlite IRA-904 resin.

EXAMPLE 3

Ten milliliters of moist Lewatit CA-9268 HL (brand name of a product of Bayer Co., Ltd., of West Germany), a strongly-basic anion exchange resin type-II, was packed in a 1.6×20 cm column. This column was then treated with 50 ml of a 2 M NaCl solution at SV 1, followed by thorough washing with water. Next, the glucose isomerase solution S prepared as described in Experimental Example 1 was employed and 3 ml (containing 5,000 U of glucose isomerase and 98 mg of polysaccharide out of a total saccharide content of 112 mg) was circulated through the above-mentioned column overnight at a flow rate of BVH 1 and room temperature.

This column was then washed with 20 ml of deionized water to remove unadsorbed matter from the resin bed. The wash solution was later analyzed for its contents of glucose isomerase activity and total saccharides, and the adsorption efficiencies for the glucose isomerase and total saccharides were calculated. The results indicated that the glucose isomerase was barely adsorbed by the Lewatit CA-9268 HL, whereas 87.9% of the total saccharides was adsorbed.

Next, 10 ml of moist Amberlite IRA-904 was packed in a 1.6×20 cm column, and this column was then washed thoroughly with deionized water. Then the glucose isomerase solution which was obtained by eliminating most of the polysaccharide from glucose isomerase solution S by treating it as previously described on a Lewatit CA-9268 HL column was employed in a volume of 15 ml (containing 3,000 U of glucose isomerase) and supplied to the Amberlite IRA-904 column and circulated through it overnight at a flow-rate of BVH1 and room temperature.

The column was then washed with 50 ml of deionized water to wash out the unadsorbed matter from the resin bed, and the wash solution was analyzed for its glucose isomerase activity. The results confirmed that 100% of the supplied glucose isomerase was adsorbed by the Amberlite IRA-904 resin.

EXAMPLE 4

Ten milliliters of moist IMAC S5-40 (brand name of a product of Shinetsu Kagaku Co., Ltd.), a strongly-basic anion exchange resin, was packed in a 1.6×20 cm column. This column was then treated with 50 ml of a 2 M NaCl solution at BVH 1, followed by thorough washing with water. Next, the glucose isomerase solution S prepared as described in Experimental Example 1 was employed and 3 ml (containing 5,000 U of glucose isomerase and 98 mg of polysaccharide out of a total saccharide content of 112 mg) was circulated through the above-mentioned column overnight at a flow-rate of BVH 1 and room temperature.

This column was then washed with 20 ml of deionized water to remove unadsorbed matter from the resin bed. The wash solution was later analyzed for its contents of glucose isomerase activity and total saccharides, and the adsorption efficiencies for the glucose isomerase and total saccharides were calculated. The results indicated that the glucose isomerase was barely adsorbed by the IMAC S5-40, whereas 88.2% of the total saccharides was adsorbed.

Next, 10 ml of moist Amberlite IRA-904 was packed in a 1.6×20 cm column, and this column was then washed thoroughly with deionized water. Then the glucose isomerase solution which was obtained by eliminating most of the polysaccharide from glucose isomerase solution S by treating it as previously described on an IMAC S5-40 column, was employed in a volume of 15 ml (containing 3,000 U of glucose isomerase) and supplied to said Amberlite IRA-904 column and circulated through it overnight at a flow-rate of BVH 1 and room temperature.

The column was then washed with 50 ml of deionized water to remove unadsorbed matter from the resin bed, and the wash solution was analyzed for its content of glucose isomerase activity. The results confirmed that 100% of the supplied glucose isomerase was adsorbed by the Amberlite IRA-904 resin.

EXAMPLE 5

Ten milliliters of moist IMAC S5-50 (brand name of a product of Shinetsu Kagaku Co., Ltd.), a strongly-basic anion exchange resin, was packed in a 1.6×20 cm column. This column was then treated with 50 ml of a 2 M NaCl solution at SV 1, followed by thorough washing with water. Next, the glucose isomerase solution S prepared as described in Experimental Example 1 was employed and 3 ml (containing 5,000 U of glucose isomerase and 98 g of polysaccharide out of a total saccharide content of 112 mg) was circulated through the above-mentioned column overnight at a flow-rate of BVH 1 and room temperature.

This column was then washed with 20 ml of deionized water to remove unadsorbed matter from the resin bed. The wash solution was later analyzed for its contents of glucose isomerase activity for total saccharides, and the adsorption efficiencies for the glucose isomerase and total saccharides were calculated. The results indicated that the glucose isomerase was barely adsorbed by the IMAC S5-50, whereas 66.9% of the total saccharides was adsorbed thereto.

Next, 10 ml of moist Amberlite IRA-904 was packed in a 1.6×20 cm column, and this column was then washed thoroughly with deionized water. Then the glucose isomerase solution, which was obtained by eliminating most of the polysaccharide from glucose isomerase solution S by treating it as previously described on an IMAC S5-50 column, was employed in a volume of 15 ml (containing 3,000 U of glucose isomerase) and supplied to said Amberlite IRA-904 column and circulated through it overnight at a flowrate of BVH1 and room temperature.

The column was then washed with 50 ml of deionized water to wash out the unadsorbed matter from the resin bed, and the wash solution was analyzed for its content of glucose isomerase activity. The results confirmed that 100% of the supplied glucose isomerase was adsorbed by the Amberlite IRA-904 resin.

COMPARATIVE EXAMPLE 1

Ten milliliters of moist Amberlite IRA-904 was packed in a 1.6×20 cm column and this was then washed thoroughly with deionized water. Next, the glucose isomerase solution S prepared as described in Experimental Example 1 was diluted to a concentration of 200 U/ml and then 15 ml (containing 3,000 U of glucose isomerase) of this solution was circulated through the above-mentioned column overnight at a flow-rate of BVH1 and room temperature.

This column was then washed with 50 ml of deionized water to remove unadsorbed matter from the resin bed. The wash solution was then analyzed for its content of glucose isomerase activity.

The results indicated that only a low level, that is 44.4% of the glucose isomerase was adsorbed by the Amberlite IRA-904 resin.

EXAMPLE 6

*Streptomyces olivochromogenes* (FERM 1640, ATCC 21, 114), a glucose isomerase-producing microorganism, was inoculated into one hundred 50-ml Erlenmeyer flasks containing 50 ml of liquid medium per flask. These were then shake-cultured at 30° C. for 48 hours.

All of these culture fluids were pooled and the mycelia were collected by centrifugation at 10,000 rpm for 20 minutes. Determination was then made of the total wet cell weight, the moisture content, the dry weight, and the glucose isomerase activity following ultrasonication. The values obtained are shown in Table 13.

TABLE 13

| | |
|---|---|
| Total Wet Cell Weight | : 278 g |
| Moisture Content | : 219 g |
| Dry Cell Weight | : 59 g |
| Glucose Isomerase Activity per 1 g of Wet Cells | : 261 U |

250 g of wet cells were placed in a 1-liter Erlenmeyer flask and suspended in 750 ml of deionized water. Then 50 mg of lysozyme (0.02% relative to the wet cells; a product of Behringer Manheim Co.) and 10 ml of toluene were added and lysis was allowed to occur while stirring this mixture gently at 30° C. for 24 hours. The lyzate was then centrifuged for 20 minutes at 15,000 rpm and the precipitated cellular debris was eliminated.

The supernatant was called glucose isomerase solution T, and determination was made of its glucose isomerase activity, its total saccharide content, and, after carrying out dialysis of the solution for one night, its polysaccharide content. The values obtained are shown in Table 14 below.

TABLE 14

| Analysis of Glucose Isomerase Solution T | | | |
|---|---|---|---|
| Volume | : | 948 | ml |
| GI Activity Concentration | : | 68.77 | U/ml |
| GI Total Activity | : | 64,994 | U |
| Total Saccharide Amount | : | 1,601 | mg |
| Total Polysaccharide Amount | : | 1,298 | mg |
| Polysaccharide/GI | : | 19.97 | $\gamma/U$ |

Next, 200 ml of this glucose isomerase solution T (this volume contained 13,754 U of glucose isomerase and a total saccharide value of 337.76 mg) was placed in a 400-ml beaker. Cold isopropanol was slowly added in a volume of 112.5 ml while stirring. (The final concentration of the isopropanol was 36% by vol.) The stirring was continued for 1 hour at 4° C. and then the mixture was centrifuged for 15 minutes at 15,000 rpm. The supernatant was decanted and discarded, while the precipitated material was dissolved in about 30 ml of deionized water and transferred to a 50-ml volumetric flask. The volume of this was made up to 50 ml with deionized water and then the glucose isomerase activity and the total saccharide content of this solution were determined. It was found that the recovery of the glucose isomerase was 95.67% while the recovery of the total saccharides was 8.24%. The ratio of the total saccharide content to the glucose isomerase activity was 2.12 ($\gamma/U$).

Next, 10 ml of moist Amberlite IRA-904 was packed in a 1.6×20 cm column and then 12 ml (containing 3,158 U of glucose isomerase) of the enzyme solution prepared as described above by treating glucose isomerase solution T with isopropanol at a concentration of 36% by vol. was supplied to this column and circulated through it overnight at a flow-rate of BVH1 and room temperature. 100% of the supplied glucose isomerase activity was adsorbed by this Amberlite IRA-904 column.

EXAMPLE 7

The glucose isomerase solution T prepared in Example 6 was employed and 200 ml (containing 13,754 U of glucose isomerase and 337.76 mg of saccharides) of this was placed in a 400-ml beaker. Cold acetone was slowly added in a volume of 100 ml (giving a final acetone concentration of 33.3%) while stirring. The stirring was continued for 1 hour at 4° C. and then the mixture was centrifuged for 15 minutes at 15,000 rpm. The supernatant was decanted and discarded, while the precipitated material was dissolved in about 30 ml of deionized water and transferred to a 50-ml volumetric flask. The volume of this was made up to 50 ml with deionized water and then the glucose isomerase activity and the total saccharide content of this solution were determined. It was found that the recovery rate was 97.59% for the glucose isomerase, while the recovery rate of the total saccharides was 11.63%. The amount of total saccharide per unit of glucose isomerase activity was 2.93 ($\gamma/U$).

Next, 10 ml of moist Amberlite IRA-904 was packed in a 1.6×20 cm column and then 12 ml (containing 3,221 U of glucose isomerase) of the enzyme solution prepared as described above by treating glucose isomerase solution T with acetone at a concentration of 33.3% by vol. was supplied to this column and circulated through it overnight at a flow-rate of BVH1 and room temperature. 100% of the supplied glucose isomerase activity was adsorbed by this Amberlite IRA-904 column.

EXAMPLE 8

The glucose isomerase solution T prepared in Example 6 was employed and 200 ml (containing 13,754 U of glucose isomerase and 337.76 mg of saccharides) was placed in a 400-ml beaker. Cold ethanol was slowly added in a volume of 135 ml (giving a final ethanol concentration of 40.3%) while stirring. The stirring was continued for 1 hour at 4° C. and then the mixture was centrifuged for 15 minutes at 15,000 rpm. The supernatant was decanted and discarded, while the precipitated material was dissolved in about 30 ml of deionized water and transferred to a 50-ml volumetric flask. The volume of this was made up to 50 ml with deionized water and then the glucose isomerase activity and the total saccharide content of this solution were determined. It was found that the recovery rate of the glucose isomerase was 98.52%, while the recovery rate of the total saccharides was 12.03%. The amount of total saccharide per unit of the glucose isomerase activity was thus 3.00 ($\gamma/U$).

Next, 10 ml of moist Amberlite IRA-904 was packed in a 1.6×20 cm column and then 12 ml (containing 3,252 U of glucose isomerase) of the enzyme solution prepared as described above by treating glucose isomerase solution T with ethanol at a concentration of 40.3% by vol. was supplied to this column and circulated through it overnight at a flow-rate of BVH1 and room temperature. 100% of the supplied glucose isomerase activity was adsorbed by this Amberlite IRA-904 column.

EXAMPLE 9

The glucose isomerase solution T prepared in Example 6 was employed and 200 ml (containing 13,754 U of glucose isomerase and 337.76 mg of saccharides) was placed in a 400-ml beaker. A 70.2 g amount of ammonium sulfate (giving a final ammonium sulfate concentration of 55% of saturation) was added to this enzyme solution while it was being stirred. The stirring was continued for 1 hour at 4° C. and then the mixture was centrifuged for 15 minutes at 15,000 rpm. The supernatant was decanted and discarded, while the precipitated material was dissolved in about 30 ml of deionized water and transferred to a 50-ml volumetric flask. The volume of this was made up to 50 ml with deionized water and then the glucose isomerase activity and the total saccharide content of this solution were determined. It was found that the recovery of the glucose isomerase was 95.28%, while the recovery of the total saccharides was 7.35%. The amount of total saccharide per unit of the glucose isomerase activity was 1.89 ($\gamma/U$).

Next, 10 ml of moist Amberlite IRA-904 was packed in a 1.6×20 cm column and then 12 ml (containing 3,145 U of glucose isomerase) of the enzyme solution prepared as described above by treating glucose isomerase solution T with ammonium sulfate at a concentration giving 55% saturation was supplied to this column and circulated through it overnight at a flow-rate of BVH1 and room temperature. 100% of the supplied glucose isomerase activity was adsorbed by this Amberlite IRA-904 column.

COMPARATIVE EXAMPLE 2

The glucose isomerase solution T prepared in Example 6 was employed and 200 ml (containing 13.745 U of glucose isomerase and 337.76 mg of saccharides) was placed in a 1-liter beaker. Cold isopropanol was slowly added to this in a volume of 400 ml (giving a final isopropanol concentration of 66.7%) while stirring. The stirring was continued for 1 hour at 4° C. and then the mixture was centrifuged for 15 minutes at 15,000 rpm. The supernatant was decanted and discarded, while the precipitated material was dissolved in about 30 ml of deionized water and transferred to a 50-ml volumetric flask. The volume of this was made up to 50 ml with deionized water and then the glucose isomerase activity and the total saccharide content of this solution was determined. It was found that the recovery for the glucose isomerase was 98.47%, while the recovery of the total saccharides was 73.0%. The amount of total saccharide per unit of the glucose isomerase activity was 18.21 ($\gamma/U$).

Next, 10 ml of moist Amberlite IRA-904 was packed in a 1.6×20 cm column and then 12 ml (containing 3,250 U of glucose isomerase) of the enzyme solution prepared as was described above by treating glucose isomerase solution T with isopropanol at a concentration of 66.7% by vol. was supplied to this column and circulated through it overnight at a flow-rate of BVH1 and room temperature. 46.3% of the supplied glucose isomerase activity was adsorbed by this Amberlite IRA-904 column.

REFERENCE EXAMPLE 1

The immobilized glucose isomerase which was prepared in accordance with the process described in Example 1 was employed, 10 ml (moist) of this was packed in a column (1.6×20 cm). The temperature of the column was kept at 60° C.

Next, a 50% glucose solution containing 0.002 M $MgCl_2$ having a pH of 8.5 was continuously passed through the column (initially at BVH3.5) and the effluent was collected. The fructose content of the initial effluent (against DS) was 45%. The flow rate (BVH) was gradually decreased in order to maintain this level of fructose content. After 20 days, the flow rate had reached 50% of the original BVH.

REFERENCE EXAMPLE 2

The immobilized glucose isomerase prepared in accordance with the process described in Example 6 was employed, 10 ml (moist) of this was packed in a column (1.6×20 cm). The temperature of the column was kept at 60° C.

Next, a 50% glucose solution containing 0.002 M $MgCl_2$ having a pH of 8.5 was continuously passed through the column (initially at BVH3.8), and effluent was collected.

The fructose content of the initial effluent (against DS) was 45%. The flow rate (BVH) was gradually decreased in order to maintain this level of fructose content. After 22 days, the flow rate had reached 50% of the original BVH.

REFERENCE EXAMPLE 3

The immobilized glucose isomerase prepared in accordance with the process described in Example 9 was employed, 10 ml (moist) of this was packed in a column (1.6×20). The temperature of the column was kept at 70° C.

A 50% glucose solution containing 0.002 M $MgCl_2$ and having a pH of 8.5 was continuously passed through the column (at an initial flow rate of BVH6) and the effluent was collected.

The fructose content of the initial effluent was 45% (against DS). The flow rate was gradually decreased in order to maintain this level of fructose content. The flow rate had reached 50% of the original BVH after 6 days.

What is claimed is:

1. A method for the production of immobilized glucose isomerase comprising:
   (a) obtaining a crude glucose isomerase preparation containing a high molecular weight, nondialyzable polysaccharide which inhibits adsorption of said glucose isomerase on an ion exchange resin from a microorganism which produces and retains the glucose isomerase substantially intracellularly;
   (b) separating said polysaccharide from said glucose isomerase preparation to give a purified glucose isomerase essentially completely free of said polysaccharide; and then
   (c) contacting a solution of the purified glucose isomerase with an ion exchange resin to absorb and immobilize said glucose isomerase thereon, said ion exchange resin being one capable of adsorbing said polysaccharide which inhibits adsorption of said glucose isomerase.

2. The method of claim 1, wherein the glucose isomerase preparation is obtained from a Streptomyces microorganism.

3. The method of claim 2, wherein the microorganism is *Streptomyces olivochromogenes*.

4. The method of claim 1, wherein the purified glucose isomerase essentially completely free of said polysaccharide is prepared by contacting the crude preparation with an ion exchange resin which selectively adsorbs and removes polysaccharide.

5. The method of claim 4, wherein the ion exchange resin is selected from the group consisting of a strongly-basic anion exchange resin (type I); strongly-basic anion exchange resin (type II); moderately-basic anion exchange resin, or a weakly-basic anion exchange resin.

6. The method of claim 1, wherein the purified glucose isomerase essentially completely free of said polysaccharide is prepared by combining the crude preparation with an organic solvent at a concentration at which the glucose isomerase will be selectively precipitated to separate said glucose isomerase from said polysaccharide, and then redissolving said glucose isomerase.

7. The method of claim 6, wherein the organic solvent is selected from the group consisting of methanol, ethanol, propanol, isopropanol, butanol, acetone, p-dioxane and admixtures thereof.

8. The method of claim 1, wherein the purified glucose isomerase essentially completely free of said polysaccharide is obtained by combining the crude preparation with a salt at a concentration at which the glucose isomerase will be selectively precipitated to separate said glucose isomerase from said polysaccharide, and then redissolving said glucose isomerase.

9. The method of claim 8, wherein the salt is selected from the group consisting of ammonium sulfate, sodium sulfate, magnesium sulfate and admixtures thereof.

10. The immobilized glucose isomerase produced by the method of claim 1.

* * * * *